United States Patent
Durrell et al.

(10) Patent No.: US 7,571,851 B2
(45) Date of Patent: Aug. 11, 2009

(54) COMPUTERIZED SYSTEM AND METHOD FOR PROCESSING A NUMBER OF ATTACHMENTS ASSOCIATED WITH A PATIENT

(75) Inventors: Deborah J. Durrell, Kansas City, MO (US); Charles S. Fox, Jr., Leawood, KS (US); Stephanie L. Rogers, Kansas City, MO (US); Kris Kline, Kansas City, MO (US)

(73) Assignee: Cerner Innovations, Inc., Overland Park, KS (US)

( * ) Notice: Subject to any disclaimer, the term of this patent is extended or adjusted under 35 U.S.C. 154(b) by 101 days.

(21) Appl. No.: 11/351,576

(22) Filed: Feb. 10, 2006

(65) Prior Publication Data

US 2007/0187478 A1 Aug. 16, 2007

Related U.S. Application Data

(63) Continuation-in-part of application No. 10/767,319, filed on Jan. 29, 2004, now Pat. No. 7,519,541.

(51) Int. Cl.
*G06K 5/00* (2006.01)
(52) U.S. Cl. .................................. 235/382; 235/462.45
(58) Field of Classification Search ................. 235/385, 235/462.44, 462.45, 462.46, 470, 470.01, 235/472.01, 382, 462.25; 705/2, 3
See application file for complete search history.

(56) References Cited

U.S. PATENT DOCUMENTS

| | | | |
|---|---|---|---|
| 4,857,716 A | 8/1989 | Gombrich et al. | |
| 5,153,827 A | 10/1992 | Coutre et al. | |
| 5,317,506 A | 5/1994 | Coutre et al. | |
| 5,594,786 A | 1/1997 | Chaco et al. | |
| 5,682,728 A | 11/1997 | DeBusk | |
| 5,748,907 A | 5/1998 | Crane | |
| 5,781,442 A | 7/1998 | Engleson et al. | |
| 5,991,728 A | 11/1999 | DeBusk | |
| 6,085,493 A | 7/2000 | DeBusk | |

(Continued)

FOREIGN PATENT DOCUMENTS

WO 96/06944 5/1996

(Continued)

OTHER PUBLICATIONS

Office Action for U.S. Appl. No. 10/294,963 dated Apr. 24, 2008.

(Continued)

*Primary Examiner*—Daniel St. Cyr
(74) *Attorney, Agent, or Firm*—Shook, Hardy & Bacon LLP

(57) ABSTRACT

A method and system in a computerized health care environment for determining whether an attachment may be safely attached to a body site of a patient is provided. A patient identifier is received and the patient's electronic medical record is accessed. An attachment identifier is received and data for the attachment is accessed. A body site identifier identifying the area of the body of the patient to which the attachment is to be placed is received and data for the body site is accessed. Some or all of the data are used to determine whether the attachment may be safely attached to the body site of the patient.

20 Claims, 19 Drawing Sheets

U.S. PATENT DOCUMENTS

| | | | |
|---|---|---|---|
| 6,151,582 | A | 11/2000 | Huang |
| 6,519,569 | B1 | 2/2003 | White et al. |
| 6,671,563 | B1 | 12/2003 | Engelson et al. |
| 6,731,989 | B2 | 5/2004 | Engleson et al. |
| 6,790,198 | B1 | 9/2004 | White et al. |
| 6,915,170 | B2 | 7/2005 | Engleson et al. |
| 6,985,870 | B2 | 1/2006 | Martucci et al. |
| 7,096,072 | B2 | 8/2006 | Engleson et al. |
| 7,103,419 | B2 | 9/2006 | Engleson et al. |
| 7,107,106 | B2 | 9/2006 | Engleson et al. |
| 7,117,041 | B2 | 10/2006 | Engleson et al. |
| 2002/0007290 | A1 | 1/2002 | Gottlieb |
| 2002/0042725 | A1 | 4/2002 | Mayaud |
| 2002/0077850 | A1 | 6/2002 | McMenimen |
| 2002/0082866 | A1 | 6/2002 | Ladouceur |
| 2002/0188179 | A1 | 12/2002 | Bulat |
| 2002/0188469 | A1 | 12/2002 | Shalmi |
| 2003/0023500 | A1 | 1/2003 | Boies |
| 2003/0055685 | A1* | 3/2003 | Cobb et al. .................... 705/3 |
| 2003/0069774 | A1 | 4/2003 | Hoffman |
| 2003/0132249 | A1 | 7/2003 | Romano |
| 2003/0139701 | A1 | 7/2003 | White et al. |
| 2004/0044546 | A1 | 3/2004 | Moore |
| 2004/0098286 | A1 | 5/2004 | Zimmerman |
| 2005/0027563 | A1* | 2/2005 | Fackler et al. .................. 705/2 |
| 2005/0107914 | A1 | 5/2005 | Engleson et al. |
| 2005/0108140 | A1 | 5/2005 | De La Motte |

FOREIGN PATENT DOCUMENTS

| | | | |
|---|---|---|---|
| WO | WO9606944 | A1 | 7/1996 |

OTHER PUBLICATIONS

Office Action for U.S. Appl. No. 10/750,217 dated Feb. 22, 2008.
Office Action for U.S. Appl. No. 10/750,216 dated Sep. 6, 2007.
Office Action for U.S. Appl. No. 10/750,221 dated Jan. 23, 2008.
Office Action for U.S. Appl. No. 10/750,210 dated Apr. 29, 2008.
Office Action for U.S. Appl. No. 11/351,575 dated Jan. 14, 2008.
Office Action for U.S. Appl. No. 11/351,460 dated Jun. 12, 2008.

* cited by examiner

2002
ORDER DETAIL: MORPHINE:100ML IV
☑ INGREDIENT 1
☑ INGREDIENT 2

2004
2006 — PERFORM DATE/TIME:
06-16-2006   12:30  AM

2008 — SITE: ANTICUBITAL, LEFT    BAG#: 8
2009

| | ORDERED | ACTUAL |
|---|---|---|
| 2010 VOLUME(ML): | 100 | |
| 2012 RATE(ML/HR): | 10 | 5 |

SCAN PUMP: INFORMATION
2014 — ADD COMMENT...

2102  2100
2104 — ORDER DETAIL: MORPHINE:100ML IV
☑ INGREDIENT 1
☑ INGREDIENT 2

2106 — PERFORM DATE/TIME:
2108   06-16-2006   12:30   AM

WEIGHT: 100  KG
2110
2109 — SITE: ANTICUBITAL, LEFT    BAG#: 8

| 2112 | ORDERED | ACTUAL |
|---|---|---|
| VOLUME(ML): | 100 | |
| 2114 RATE(ML/HR): | 10 | 5 |
| 2116 DOSE/DOSE UNIT: | 10 MCG/MIN | 5 MCG/MIN |

SCAN PUMP: INFORMATION
2118 — ADD COMMENT...

- 2200
- 2202 — ORDER DETAIL: MORPHINE:100ML IV
- 2204
- ☑ INGREDIENT 1
- ☑ INGREDIENT 2
- 2208 — BAG#: 8
- 2206 — SITE: ANTICUBITAL, LEFT
- 2210 — INFUSE FROM: 06-16-2006  12:30  AM
- 2212 — INFUSE TO: 06-16-2006  12:30  AM

| | ORDERED | ACTUAL |
|---|---|---|
| 2214 INFUSE OVER: | 24 | |
| 2216 VOLUME(ML): | 100 | |
| 2218 RATE(ML/HR): | 10 | 100 |

SCAN PUMP: INFORMATION

ADD COMMENT...
— 2220

FIG. 23.

- 2300
- 2302 — ORDER DETAIL: MORPHINE:100ML IV
- 2304
- ☑ INGREDIENT 1
- ☑ INGREDIENT 2
- 2308 — BAG#: 8
- 2306 — WASTE VOLUME (ML): 100
- 2310 — DATE/TIME: 06-16-2006  12:30  AM

ADD COMMENT...
— 2312

FIG. 24.

- 2400
- 2402 — ORDER DETAIL: MORPHINE:100ML IV
- 2404
- ☑ INGREDIENT 1
- ☑ INGREDIENT 2
- 2406 — PERFORM DATE/TIME: 06-16-2006  12:30  AM
- 2410 — SITE: ANTICUBITAL, LEFT   BAG#: 8
- 2418 — ADD COMMENT...
— 2412

FIG. 25.

COMPUTERIZED SYSTEM AND METHOD FOR PROCESSING A NUMBER OF ATTACHMENTS ASSOCIATED WITH A PATIENT

CROSS-REFERENCE TO RELATED APPLICATIONS

The present application is a continuation-in-part of U.S. application Ser. No. 10/767,319 filed Jan. 29, 2004, now U.S. Pat. No. 7,519,541 entitled SYSTEM AND METHOD IN A COMPUTER SYSTEM FOR MANAGING A NUMBER OF ATTACHMENTS ASSOCIATED WITH A PATIENT. This application is related by subject matter to the inventions disclosed in the commonly assigned U.S. patent application Ser. No. 11/351,575, entitled "COMPUTERIZED SYSTEM AND METHOD FOR DETERMINING WHETHER A CONSUMABLE MAY BE SAFELY ADMINISTERED TO A BODY SITE OF A PATIENT" filed on Feb. 10, 2006, and U.S. patent application Ser. No. 11/351,460, entitled "COMPUTERIZED SYSTEM AND METHOD FOR DETERMINING WHETHER A LOCATION ON A PATIENT'S BODY IS AVAILABLE FOR AN ATTACHMENT" filed on Feb. 10, 2006.

STATEMENT REGARDING FEDERALLY SPONSORED RESEARCH OR DEVELOPMENT

Not applicable.

BACKGROUND OF THE INVENTION

With the shortage of skilled caregivers and the growing complexity of the healthcare industry, the potential for devastating healthcare errors has increased. Mistakes are often made during the health care process due to the sheer number of constantly changing caregivers, the growing complexity of health care, and opportunities for error. In a hospital environment, post-surgical procedures can be the most dangerous segment of a patient's hospital stay.

A number of attachments are associated with a patient in the provision of modern healthcare, particularly in a critical care or intensive care setting. As the number of attachments and functions provided by these attachments increases, the potential for adverse and other atypical events increases. For instance, particular risks include associating attachments to the wrong body site location of a patient and determining where to associate attachments.

Other risks include dispensing of medications and other consumables to a patient in an institutional environment. For instance, a medication or other consumable may be administered via an attachment to the incorrect body site of a patient.

A solution is needed for managing healthcare that is both safe and efficient. The solution should decrease the efforts and steps required of caregivers in order to minimize the opportunity for error.

BRIEF SUMMARY OF THE INVENTION

In one embodiment, a method in a computerized health care environment for determining whether an attachment may be safely attached to a body site of a patient is provided. A patient identifier to identify a patient is received and the patient's electronic medical record is accessed. An attachment identifier identifying an attachment is received and data for the attachment are accessed. A body site identifier identifying the area of the body of the patient to which the attachment is to be placed is received and data for the body site are accessed. The data are utilized to determine whether the attachment may be safely attached to the body site of the patient.

In another embodiment a computerized system for collecting data from a patient identifier, an attachment identifier, and a body site identifier is provided. The system comprises a central information system containing patient data, attachment data and body site data. The system further comprises a patient identifier linking a patient to patient data in the central information system, an attachment identifier linking the attachment to attachment data in the central information system, and a body site identifier identifying a body site location on the patient and linking the site to location data in the central information system. The system includes a portable information device for collecting the patient identifier, the attachment identifier and the body site identifier and communicating with the central information system to access the patient data, attachment data and body site data.

In yet another embodiment, a method of retrieving and transmitting patient data in a computerized environment is provided. A patient identifier is retrieved with a portable information device, wherein the patient identifier identifies a patient. An attachment identifier is retrieved with a portable information device, wherein the attachment identifier identifies an attachment. A body site identifier is retrieved with a portable information device, wherein the body site identifier identifies a location for the attachment on the patient's body. The patient identifier, the attachment identifier and the body site identifier are transmitted to a central information system. Current patient related information is received from the central information system at the portable information device.

BRIEF DESCRIPTION OF THE DRAWINGS

The present invention is described in detail below with reference to the attached drawings figures, wherein:

FIGS. 12-27 illustrate screen displays in accordance with embodiments of the invention.

DETAILED DESCRIPTION OF THE INVENTION

Embodiments of the present invention are directed to a system and method for managing patient care in a safe manner so as to minimize caregiver error and maximize efficiency. Having briefly provided an overview of the present invention, embodiments of the invention will be discussed with reference to FIGS. 1-27.

Figure 1:
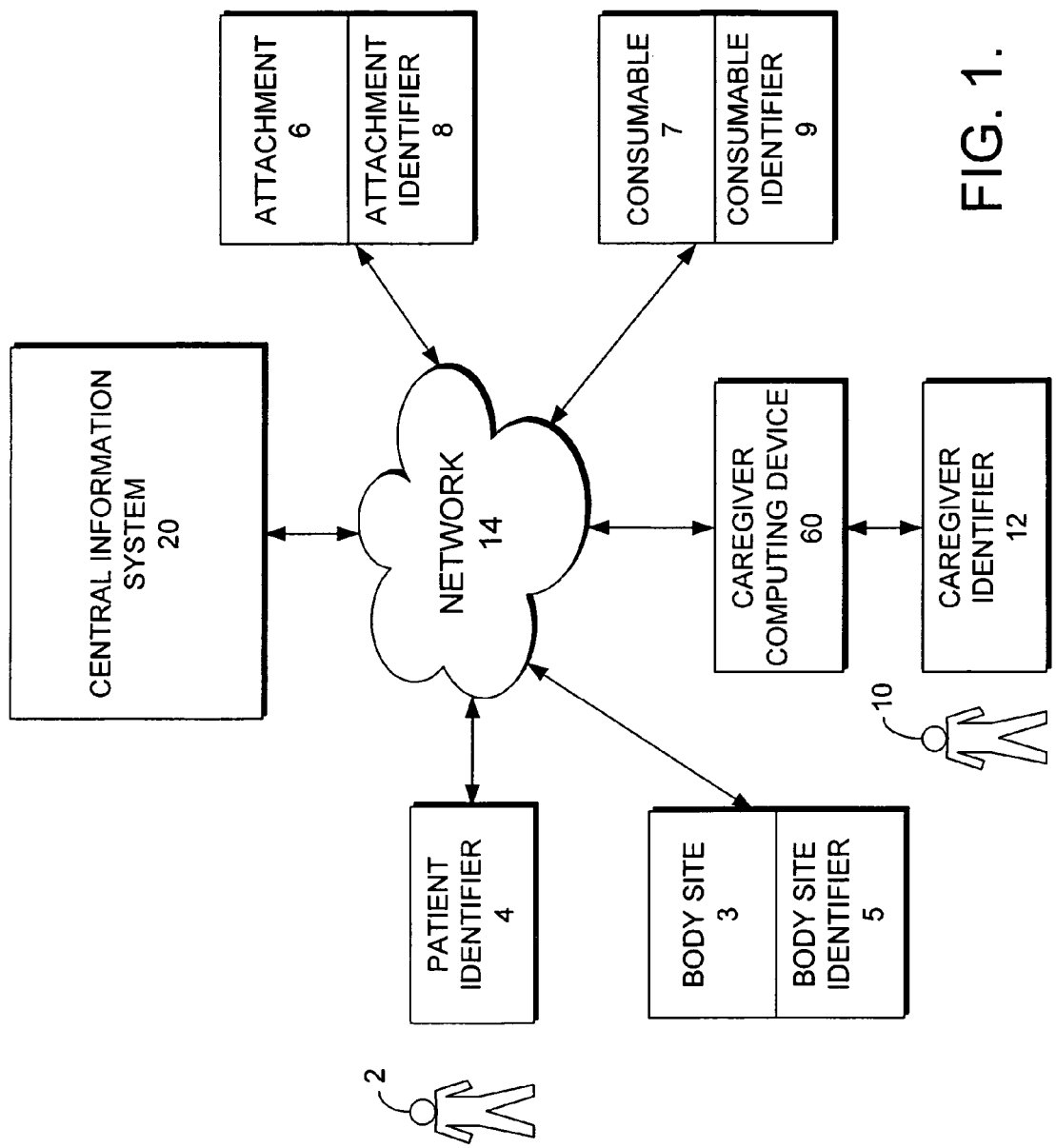
FIG. 1 is a block diagram illustrating components of a system for managing patient care in accordance with an embodiment of the invention.

Specifically, with initial reference to FIG. 1, a patient identifier 4 may identify a patient 2 and an attachment identifier 8 may identify an attachment 6. A caregiver identifier 12 may identify a caregiver 10. A body site identifier 5 may identify a body site 3 and a consumable identifier 9 may identify a consumable 7. A central information system 20 and a caregiver portable computing device 60 are capable of communicating over a network 14. The caregiver portable computing device 60 is also capable of processing information from the patient identifier 4, the body site identifier 5, the attachment identifier 8, the consumable identifier 9 and the caregiver identifier 12. The caregiver portable computing device 60 can transmit the information to the central information system 20. In this manner, each caregiver 10, each patient 2, each body site 3, each attachment 6 and each consumable 7 can be transmitted to the central information system 20. Although all components are shown as communicating over the network 14, peer-to-peer communication may also be possible. Also, while the components are shown in communication with the central information system, a distributed system may be possible. Each of the components of the system is described in greater detail below.

Figure 3:
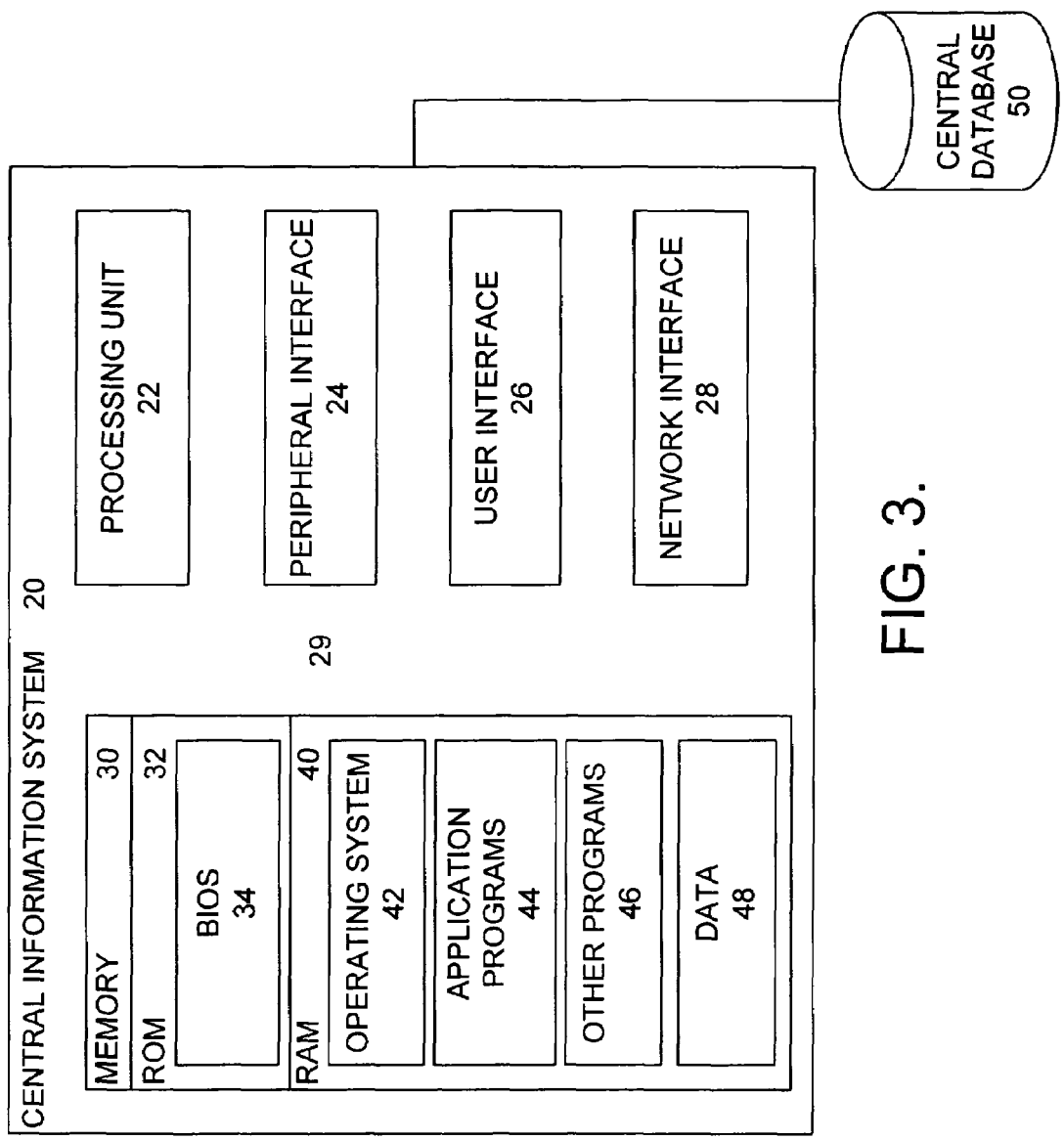
FIG. 3 is a block diagram illustrating components of a central information system in accordance with an embodiment of the invention.

FIG. 3 illustrates an embodiment of the central information system 20. The central information system 20 may include a processing unit 22, a peripheral interface 24, a user interface 26, and a network interface 28. The central information system 20 may also include a memory 30. A system bus 29 couples the aforementioned components. The central information system 20 may also include a central database 50.

The system memory 30 may include computer storage media in the form of volatile and/or nonvolatile memory such as read only memory (ROM) 32 and random access memory (RAM) 40. A basic input/output system 34 (BIOS), containing the basic routines that help to transfer information between elements within the central information system 20, such as during start-up, is typically stored in ROM 32. RAM 40 typically contains data and/or program modules that are immediately accessible to and/or presently being operated on by processing unit 22.

By way of example, and not limitation, FIG. 3 illustrates operating system 42, application programs 44, other program modules 46, and program data 48. The application programs 44 and other programs 46 may be described in the general context of computer-executable instructions, such as program modules, being executed by a computer. The applications programs 44 include components for matching patient data, caregiver data, and medication data in the central database 50 with identifiers transmitted by the caregiver portable computing device 60 (FIG. 1). Furthermore, the application programs 44 include components for generating a patient task list. The task lists are based upon knowledge databases in the central information system 20 that dictate a particular course of care. These tasks lists may be contained within the patient records 54 and the caregiver records 58 that are described below with reference to FIG. 4. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like.

The central information system 20 may also include other removable/non-removable, volatile/nonvolatile computer storage media. A hard disk drive may be provided that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive is typically connected to the system bus through a non-removable memory interface and magnetic disk drive and optical disk drive are typically connected to the system bus by a removable memory interface.

A user may enter commands and information into the central information system through the user interface 26 using input devices such as a keyboard and pointing device, commonly referred to as a mouse, trackball or touch pad. Other input devices may include a microphone, satellite dish, scanner, or the like. These and other input devices are often connected to the processing unit 22 through a user input interface 26 that is coupled to the system bus 29, but may be connected by other interface and bus structures, such as a parallel port or a universal serial bus (USB). A monitor or other type of display device may also be connected to the system bus 29 via an interface, such as the peripheral interface 24. In addition to the monitor, computers may also include other peripheral output devices such as speakers and printer.

The illustrated central information system 20 is merely an example of a suitable environment for the system of the invention and is not intended to suggest any limitation as to the scope of use or functionality of the invention. Neither should the central information system 20 be interpreted as having any dependency or requirement relating to any one or combination of components illustrated.

In embodiments, the central information system 20 in the present invention operates in a networked environment in conjunction with the network 14 as illustrated in FIG. 1, using logical connections to one or more remote computers, such as the caregiver portable computing device 60. As further described below, the caregiver portable computing device 60 may be a personal computer, and typically includes many of the elements described above relative to the central information system 20.

The network 14 may be the Internet and all components of the system may be accessible over the Internet. Logical connections for networking may include a local area network (LAN) or a wide area network (WAN), but may also include other networks. When used in a LAN networking environment, the central information system 20 may be connected to the LAN through the network interface 28 or adapter. When used in a WAN networking environment, the central information system 20 typically includes a modem or other means for establishing communications, such as the Internet. The modem, which may be internal or external, may be connected to the system bus 29 via the user input interface 26, or other appropriate mechanism.

Figure 4:
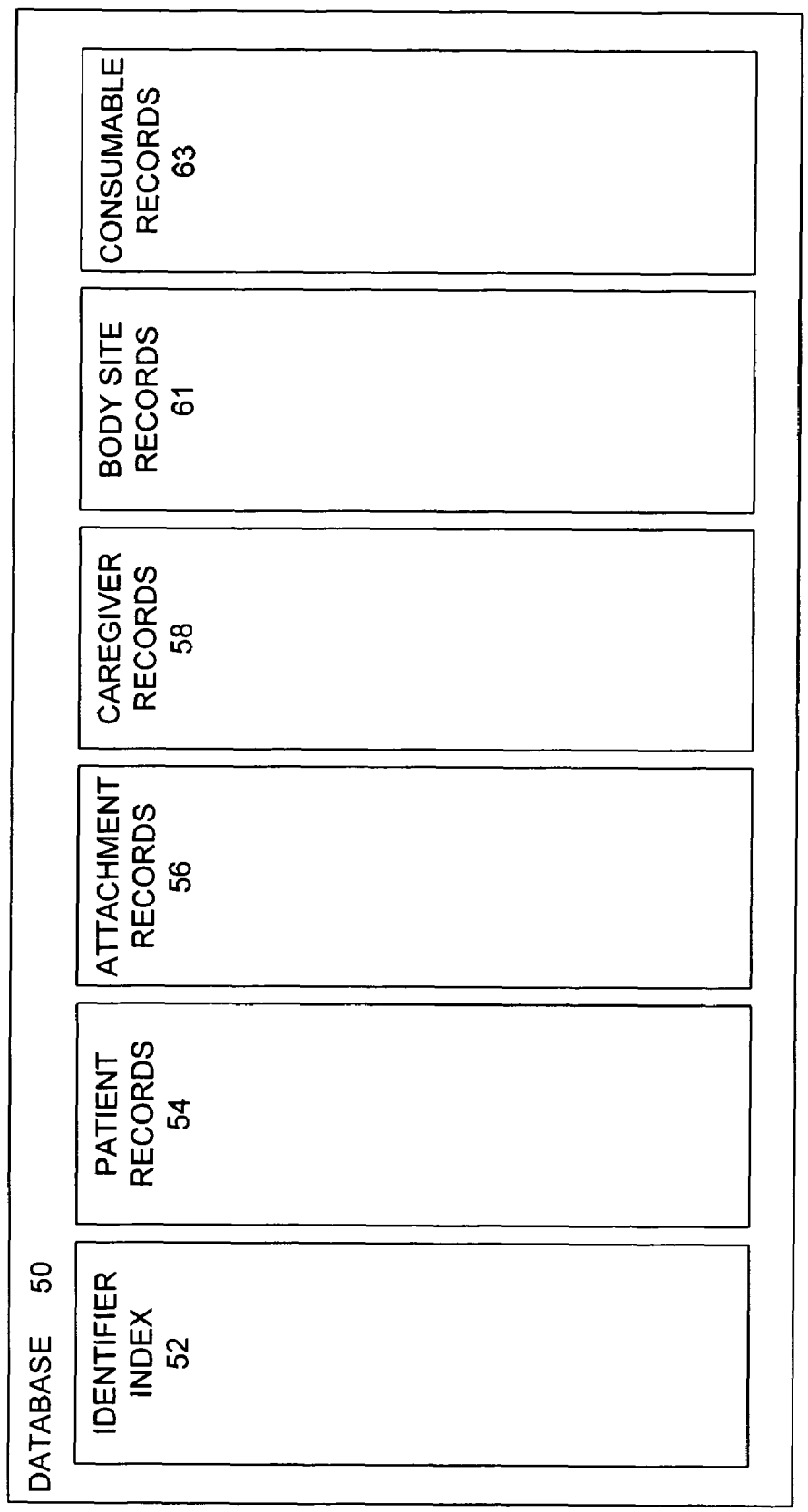
FIG. 4 is a block diagram illustrating a central database of the central information system in accordance with an embodiment of the invention.

FIG. 4 illustrates an embodiment of the central database 50 that is a component connected with the central information system 20. The central database 50 may include an identifier index 52 linking the identifiers to all of the identified patients, attachments, sites, consumables, and caregivers. In the illustrated embodiment, the identifiers are barcodes and the identifier index 52 is a barcode index. However, the identifiers may include an RF identifier (RFID) or any machine readable identifier. Additionally, the central database 50 may include patient records 54, attachment records 56, caregiver records 58, body site records 61 and consumable records 63. The patient records 54 may include each patient's treatment history, demographic information and orders entered by a physician for treatment of each patient. The attachment records 56 may include device settings and capabilities, type of attachment, date and time of insertion and removal of attachment, monitoring status, subsidiaries of attachments (e.g. lumens), calibration information, waveform status, trouble shooting data, current and prior consumables being administered via the attachment, volume, rate order details, pump information, backpress, bag data and other data relating to the attachment. The caregiver records 58 may include records of assigned tasks for each caregiver in the system. Body site records include the location of the body site on the patient, site dressing data, dressing type, site assessment and availability of the site. Consumable records may include type of consumable (e.g. medication, intravenous fluid), amount, time for administration, dosage/amount to be administered. The orders and other information can be accessed through the caregiver portable computing device 60 to determine appropriate tasks to be performed on an identified patient.

Figure 5:
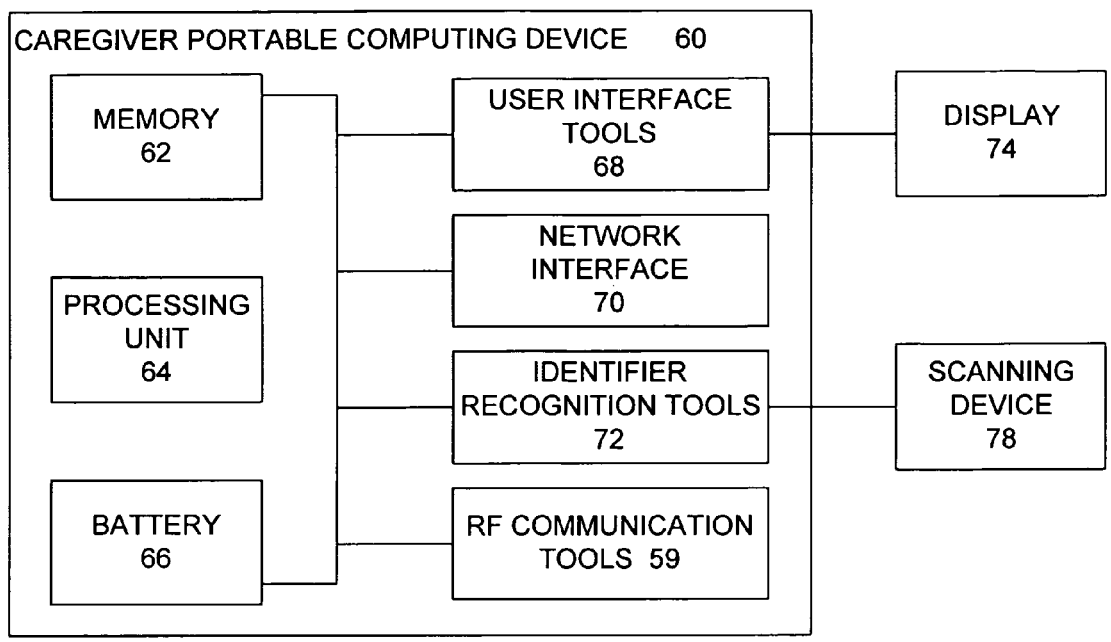
FIG. 5 is a block diagram illustrating a caregiver portable computing device in accordance with an embodiment of the invention.

FIG. 5 illustrates an exemplary embodiment of the caregiver portable computing device 60. The caregiver portable computing device 60 may include a memory 62, a processing unit 64, a battery 66, user interface tools 68, network interface 70, RF communication tools 59, and identifier recognition tools 72. The user interface tools 68 may advantageously be accessible through a built-in display device 74. The identifier recognition tools 72 may be connected with a scanning device 78 such as an embedded barcode scanner.

In an embodiment of the invention the caregiver portable computing device 60 is a handheld personal digital assistant (PDA). The PDA puts the data of the central database 50 in the caregiver's hands at the point of care. The PDA recognizes identifiers associated with the patient 2, caregiver 10, attachment 6, body site 3 and consumable 7. The PDA prompts the caregiver 10 for necessary actions and information during the care-giving process.

The caregiver portable computing device 60 is used as verification device and in an embodiment of the invention is a barcode scanner for the patient identifier 4, body site identifier 5, attachment identifier 8, consumable identifier 9 and the caregiver identifier 12. Caregivers may be provided with varying access levels. For instance, a physician may be able to enter tasks, but some less skilled caregivers may not be permitted such a high access level. In this instance, the caregiver portable computing device 60 is capable of verifying access level through the central database 50 and the caregiver identifier 12.

The caregiver portable computing device 60 accesses the central information system 20 through the network interface 70 and prompts caregivers for scheduled tasks, alerts them to potential error, facilitates documentation, and allows caregivers to review data before posting it to central database. Real time updates and current access orders are available through the caregiver portable computing device 60 in real time. While the invention is described in the context of a portable device, in embodiments, a bedside computer may be utilized alone or in combination with a scanner or other identifier.

Figure 6:
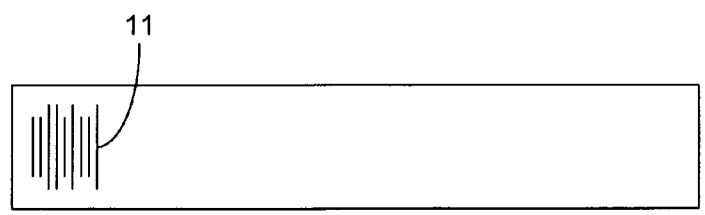
FIG. 6 is a diagram illustrating an identifier in accordance with an embodiment of the invention.

FIG. 6 illustrates an embodiment of the patient identifier 4 including an identifier 11. The identifier 11 is preferably in machine-readable form and may be a scannable barcode or RFID. The patient identifier 4 may be in the form of a patient wristband. The caregiver identifier 12 may be affixed to a caregiver badge in an embodiment of the invention. In embodiments, the body site identifiers 3, the attachment identifiers 8 and consumable identifiers 9 also include a machine-readable identifier as shown. The aforementioned identifiers are linked to specific data within the central information system database 50.

A number of consumables, attachments and body sites used in medical treatment of a patient may be labeled with an identifier such as a barcode. Any item that can be tagged with an identifier can be monitored by the system of the invention. For instance, a consumable IV bag coming from the pharmacy including medications can be labeled at the pharmacy with an identifier such as a barcode. In practice, the caregiver would scan the labeled medication before adding it to a pump. The labeled consumable may be compared with the patient identifier 5 and tasks on patient record such as the ordered dose, timing, and pump setting. The tubing attached to the pump and IV bag may also receive an identifier. Since the body site can also be labeled with an identifier, the system, through the caregiver portable computing device 60 looks for a body site to associate with the identified IV bag. The system compares the body site and the consumable to determine if the consumable may be safely administered to the body site. In this instance, the caregiver portable computing device 60 could provide a green light if all the conditions are correct and safe or an alert if it is not. Any of a number of other medical attachments that are attached, inserted, laid upon or otherwise physically associated with a patient may receive an identifier. These devices include a peripheral IV, a central line, a PA catheter, an arterial line, temporary pacemaker wires, epidural catheters, subdural catheters, endotracheal tubes, chest tubes, surgical drains and urinary catheters and implantable devices such as VP shunts, tracheostomies, cardiac pacemakers, medication pumps, implanted central lines, dialysis shunts and vascular filters. Thus, the attachment type may be identified by the physical connection or the medical device associated with connection. Likewise, the products associated with these devices may also be identified and used similarly to the pump-IV medication combinations described herein.

Labeling each component with an identifier provides a physical structure to make attachments, body sites and consumables part of the care environment and part of the workflow. If more than one attachment, body site or consumable is present, the system is capable of distinguishing them from one another because of the aforementioned identifiers. This reduces the likelihood of errors, particularly when used in conjunction with the central information system of the present invention.

Figure 2:
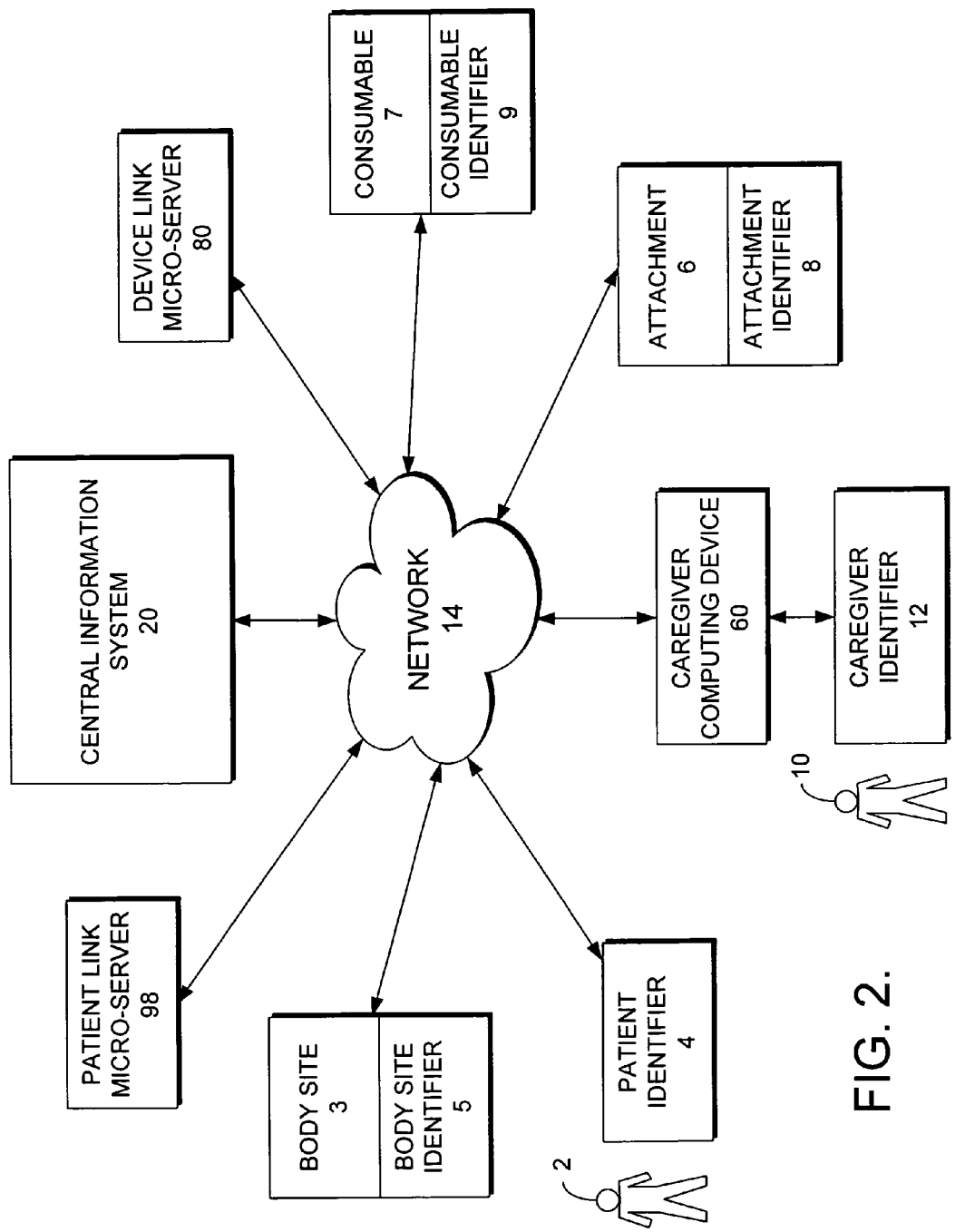
FIG. 2 is a block diagram illustrating components of a system for managing patient care in accordance with an alternative embodiment of the invention.

In another embodiment of the system of the invention, with reference to FIG. 2, additional components may be included such as a device link micro-server and a patient link micro-server 98. In implementing the system of the invention, these micro-server components 98 and 80 may both be included or either component 98 or 80 may selectively be implemented.

Figure 7:
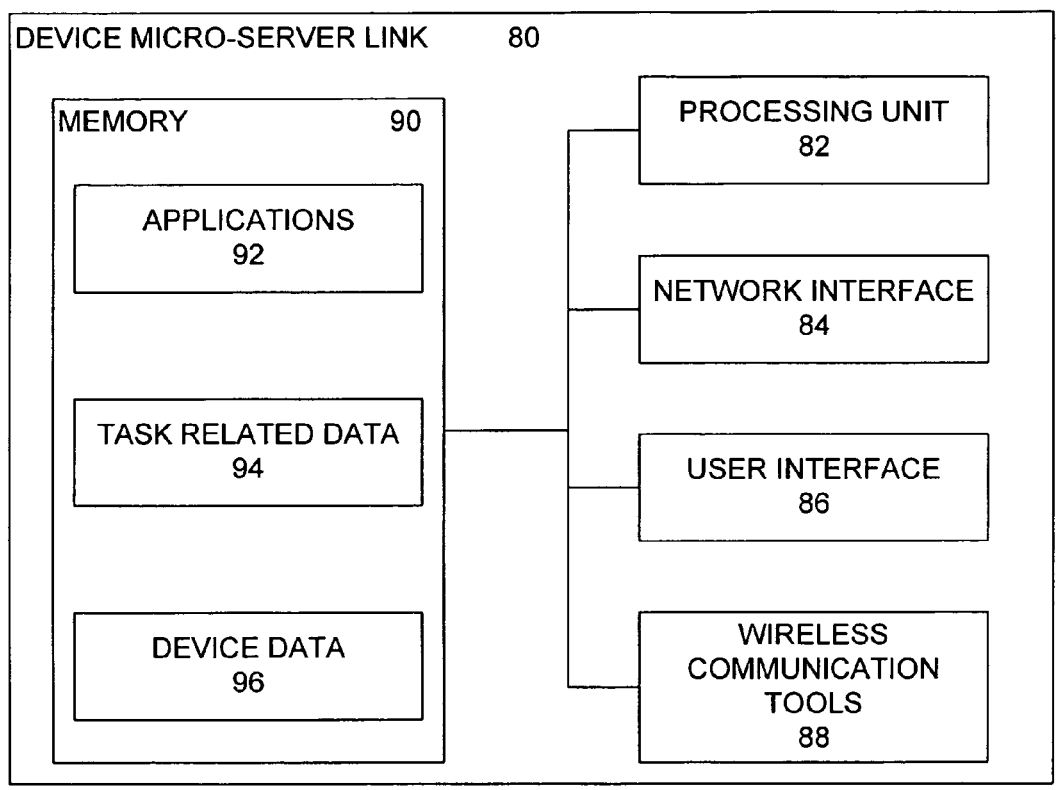
FIG. 7 is a block diagram illustrating a device link microserver in accordance with an embodiment of the invention.

FIG. 7 illustrates an embodiment of the device link micro-server 80. The device link micro-server 80 may include a processing unit 82, a network interface 84, a user interface 86, and wireless or wired communication tools 88. The device link micro-server 80 may also include a memory 90 including applications 92, task related data 94, and device data 96. The device link micro-server 80 has a device driver within its applications 92 and is capable of determining an appropriate communication protocol for the attached device. The device link micro-server 80 uses standard language protocols to communicate with any device and then converts that information to an appropriate format for user by central information system 20. Although all components are shown as communicating over the network 14, peer-to-peer communication may also be possible.

The patient link micro-server 98 may be substantially identical in structure to the device link micro-server 80 and performs a similar function. However, the application programs running on the two devices may differ. The patient link micro-server 98 and the device link micro-server 80 provide caching or local storage of data. The infrastructure of the micro-server devices 80 and 98 allows retention of data and management at nursing unit level. Data in the micro-servers 80 and 98 may be stored as tagged extensible mark-up language (XML) data.

Both the patient link micro-server 98 and the device link micro-server 80 are capable of functioning as web servers. In one embodiment, the patient link micro-server 98 communicates with the central database 50 via XML but may also support HL7 and could be configured to operate using the Cerner Millennium® architecture of Cerner Corporation of Kansas City, Mo., or in any appropriate manner in the context of the provided central information system 20. The patient link micro-server 98 stores a snapshot of all information about the associated patient, thus providing back up in case information in the central database 50 becomes inaccessible. The patient link micro-server 98 is capable of functioning as a link between the central database 50 and the processing surrounding care for the patient 2.

The caregiver portable computing device 60 with the embedded barcode scanner or other identifier recognition mechanism is capable of communication with the device link micro-server 80 and the patient link micro-server 98 with an RF signal. Both devices can communicate over the network 14 with the central information system 20 that supplies primary patient-specific information to the patient link micro-server device 98 while the central information system 20 is available.

The micro-servers 80 and 98 are capable of functioning continuously during downtime of the central information system 20 and have the ability to automatically re-synchronize with the central information system 20 when it becomes available. The patient link micro-server 98 receives updates from the central information system 20 based on design criteria and sends updates to the central information system 20 regarding patient activity and acquired device data. Further, the patient link micro-server 98 stores a record of activity performed at the bedside and any data provided to it by adjacent device link micro-servers 80. In the absence of the central information system 20, the patient link micro-server 98 will continue to check activities against its most current activity list and will queue activity updates and data until the central information system 20 signals its availability to accept those updates.

Figure 8:
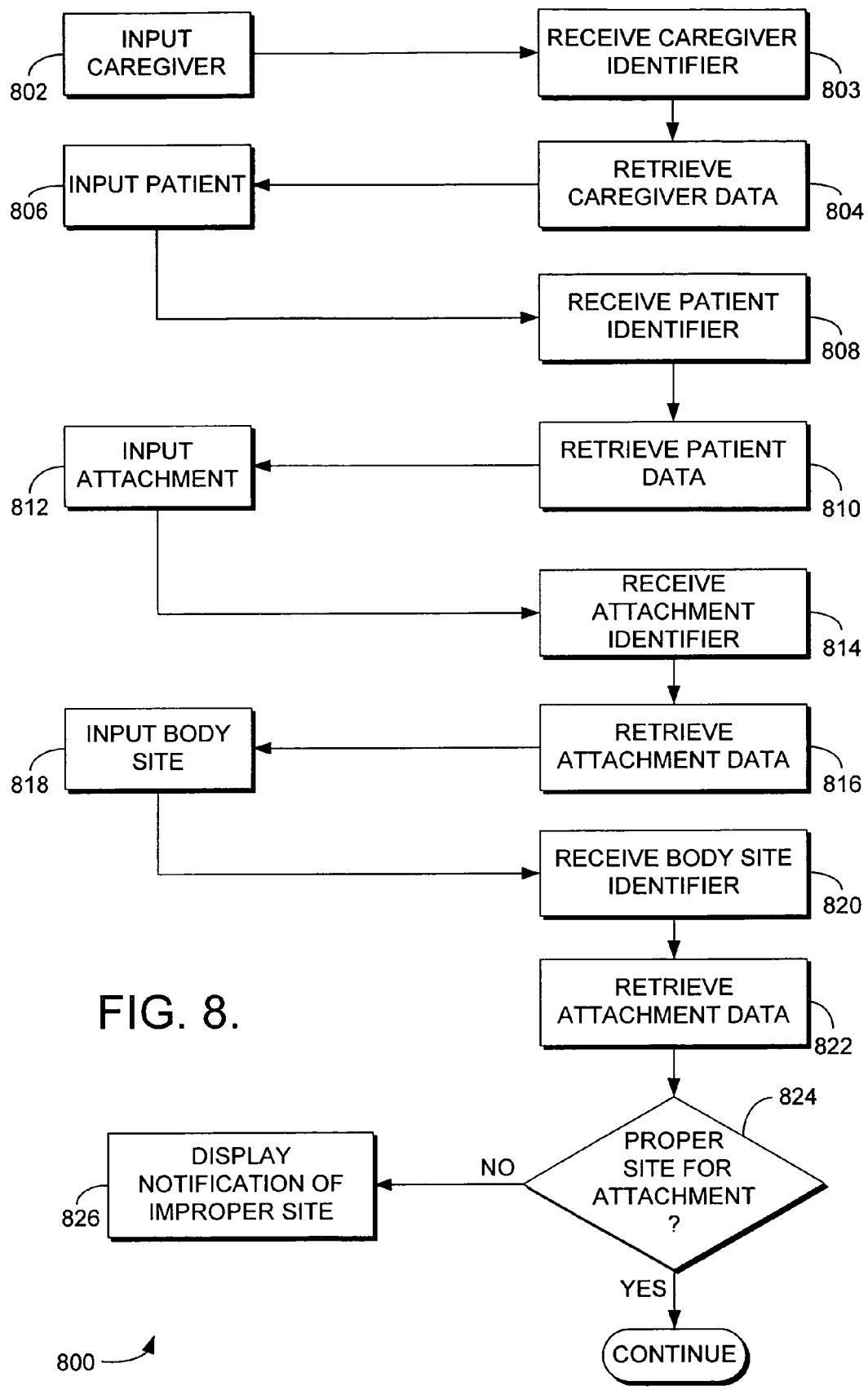
FIG. 8 is a flow chart illustrating a method for determining whether a patient body site is proper for an attachment in accordance with an embodiment of the invention.

With reference to FIG. 8, a method 800 in a computerized healthcare environment for determining whether an attachment may be safely attached to a body site of a patient is shown. FIG. 8 illustrates further details of a method for using the system of the invention in a healthcare environment. At step 802, the caregiver identification is input into the system. In one embodiment, the caregiver performs self-authentication by scanning the caregiver identifier with the caregiver portable computing device. As set forth above, this step may involve swiping or sensing a barcode, RFID, or other machine readable identifier on the caregiver security badge. This identifies the caregiver. At step 803, the caregiver identifier is received by the central information system. At step 804, verification to determine whether the caregiver is authorized to access information about the patient is performed.

At step 806, the patient is identified and input. In one embodiment the caregiver scans the patient identifier with the caregiver portable computing device. This step may involve swiping or sensing a barcode, RFID, or other machine readable identifier. In one embodiment, the identifier may be located on a patient identification bracelet or on a patient link micro-server. At step 808, the patient identifier is received by the central information system. At step 810, patient information is accessed or retrieved. The patient information may be contained in a patient's electronic medical record. Patient information may include without limitation each patient's treatment history, demographic information and orders entered by a physician for treatment of each patient At step 812, the attachment is identified and input. In one embodiment, a caregiver scans the attachment identifier with the caregiver portable computing device. Attachments include any number of medical devices that are attached, inserted, laid upon or otherwise physically associated with a patient. These attachments include a peripheral IV, a central line, a PA catheter, an arterial line, temporary pacemaker wires, epidural catheters, subdural catheters, endotracheal tubes, chest tubes, surgical drains, IV pump, urinary catheters and implantable devices such as VP shunts, tracheostomies, cardiac pacemakers, medication pumps, implanted central lines, dialysis shunts and vascular filters. The attachment may be labeled with a barcode, RFID, or other machine readable identifier that can be scanned or sensed by the caregiver portable computing devices.

At step 814, the attachment identifier is received by the central information system. At step 816, attachment information is accessed or retrieved. The attachment information may include device settings and capabilities, type of attachment, date and time of insertion and removal of attachment, monitoring status, subsidiaries of attachments (e.g. lumens), calibration information, waveform status, trouble shooting data, current and prior consumables being administered via the attachment, volume, rate order details, pump information, backpress, bag data and other data relating to the attachment.

At step 818, the body site location for associated an attachment with the patient is received. In one embodiment, the caregiver scans the body site identifier with the caregiver portable computing device. The body site includes a location or area on the patient's body where the attachment is to be attached, inserted, laid upon or otherwise physically associated with the patient. At step 820, the body site identifier is received by the central information system. At step 822, information regarding the body site is accessed. The body site information may include the location of the body site on the patient, site dressing data, dressing type, site assessment and availability of the site.

At 824, it is determined whether the attachment identified may be properly or safely attached, inserted, laid upon or physically associated with the identified body site of the patient. For example, it may be determined that the identified attachment, such as the pulmonary artery catheter of FIG. 15, may not be properly or safely physically associated with the body site 1206 of FIG. 12 for the patient because a pulmonary artery catheter may not be placed in a peripheral body site and must be placed central body site, such as central body site 1208 of FIG. 12. Alternatively, it may be determined that the identified attachment, such as peripheral venous catheter of FIG. 15, may not be safely associated with body site 1210 of FIG. 12 for the patient due to the patient's medical condition or other attachments associated with the identified body site for the patient.

At step 826, if the attachment may not be properly or safely associated with the body site of the patient, the caregiver portable computing device displays notification of such. The notification may be in the form an alert or alarm. If the caregiver chooses to override the notification, the caregiver scans the caregiver identifier and provides an explanation. The caregiver's override is received by the central information system and the override information is stored. If the attachment may be properly or safely associated with the body site of the patient, the system can continue without notification or may notify the caregiver on the caregiver portable computing device.

Figure 9:
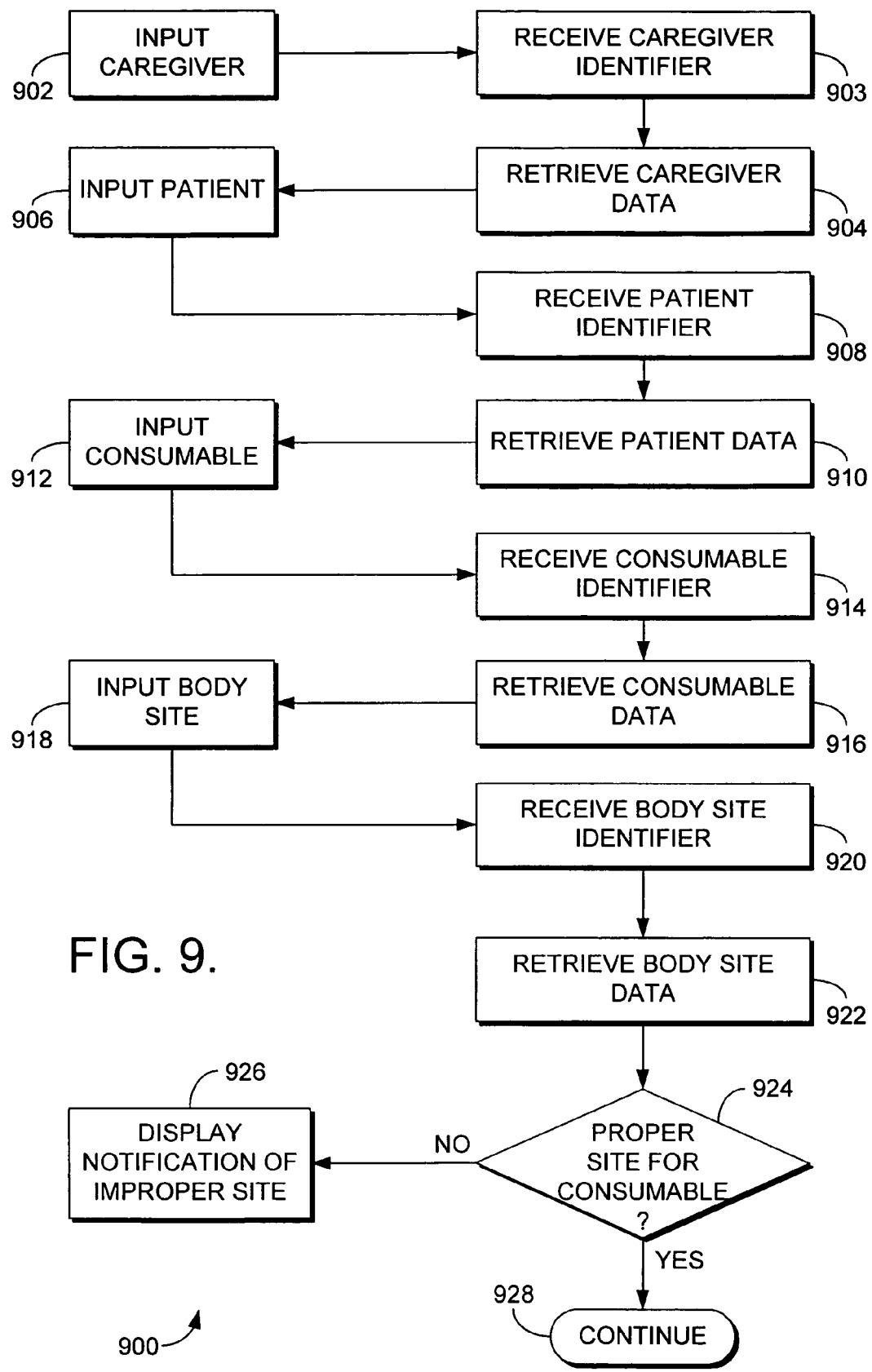
FIG. 9 is a flow chart illustrating a method for determining whether a patient body site is proper for administering a consumable in accordance with an embodiment of the invention.

With reference to FIG. 9, a method 900 in a computerized healthcare environment for determining whether a consumable may be safely administered to a body site of a patient is shown. FIG. 9 illustrates further details of a method for using the system of the invention in a healthcare environment. At step 902, the caregiver performs self-authentication by scanning the caregiver identifier with the caregiver portable computing device. As set forth above, this step may involve swiping or sensing a barcode, RFID, or other machine readable identifier on the caregiver security badge. This identifies the caregiver. At step 903, the caregiver identifier is received by the central information system. At step 904, verification to determine whether the caregiver is authorized to access information about the patient is performed.

At step 906, the caregiver scans the patient identifier with the caregiver portable computing device. This step may involve swiping or sensing a barcode, RFID, or other machine readable identifier. In one embodiment, the identifier may be located on a patient identification bracelet or on a patient link micro-server. At step 908, the patient identifier is received by the central information system. At step 910, patient data are accessed. The patient information may be contained in a patient's electronic medical record.

At step 912, the caregiver scans a consumable identifier with the caregiver portable computing device. This step may involve swiping or sensing a barcode, RFID, or other machine readable identifier. In one embodiment, the identifier is attached to the packaging of the consumable. The consumable identifier is received at step 914 and information for the consumable is accessed at step 916. The consumable information may include the type of consumable (e.g. medication, intravenous fluid), amount, time for administration, dosage/amount to be administered.

At step 918, a body site location is identified. The body site location may be identified in a variety of ways including input by the caregiver into the system and swiping or sensing a barcode, RFID, or other machine readable identifier identifying the body site location with the caregiver portable computing device. For instance, a caregiver may have scanned a barcode, RFID or other machine readable identifier and associated it with a body site location for the patient. Later, when the identifier is scanned with the caregiver portable computing device the system will associate the body site identifier with the correct body site location for the patient. The identifier to be scanned by the caregiver portable computing device may be attached to or near the body site location.

At step 920 the body site identifier is received and data related to the body site are retrieved at step 922. At step 924, it is determined whether the consumable may be properly or safely administered to the scanned body site of the patient. For example, it may be determined that the identified consumable is an inotropic drug that may not be properly or safely physically administered to the peripheral body site 1206 of FIG. 12 for the patient because a peripheral site is contraindicated for inotropic drugs.

At step 926, if the consumable may not be properly or safely administered with the body site of the patient, the caregiver portable computing device displays notification or otherwise communicates the safety issue to the caregiver. The notification may be in the form an alert or alarm. If the caregiver chooses to override the notification, the caregiver scans the caregiver identifier. The caregiver's override is received by the central information system and the override information is stored. If the attachment may be properly or safely associated with the body site of the patient, the system can continue without notification or may notify the caregiver on the caregiver portable computing device.

Figure 10:
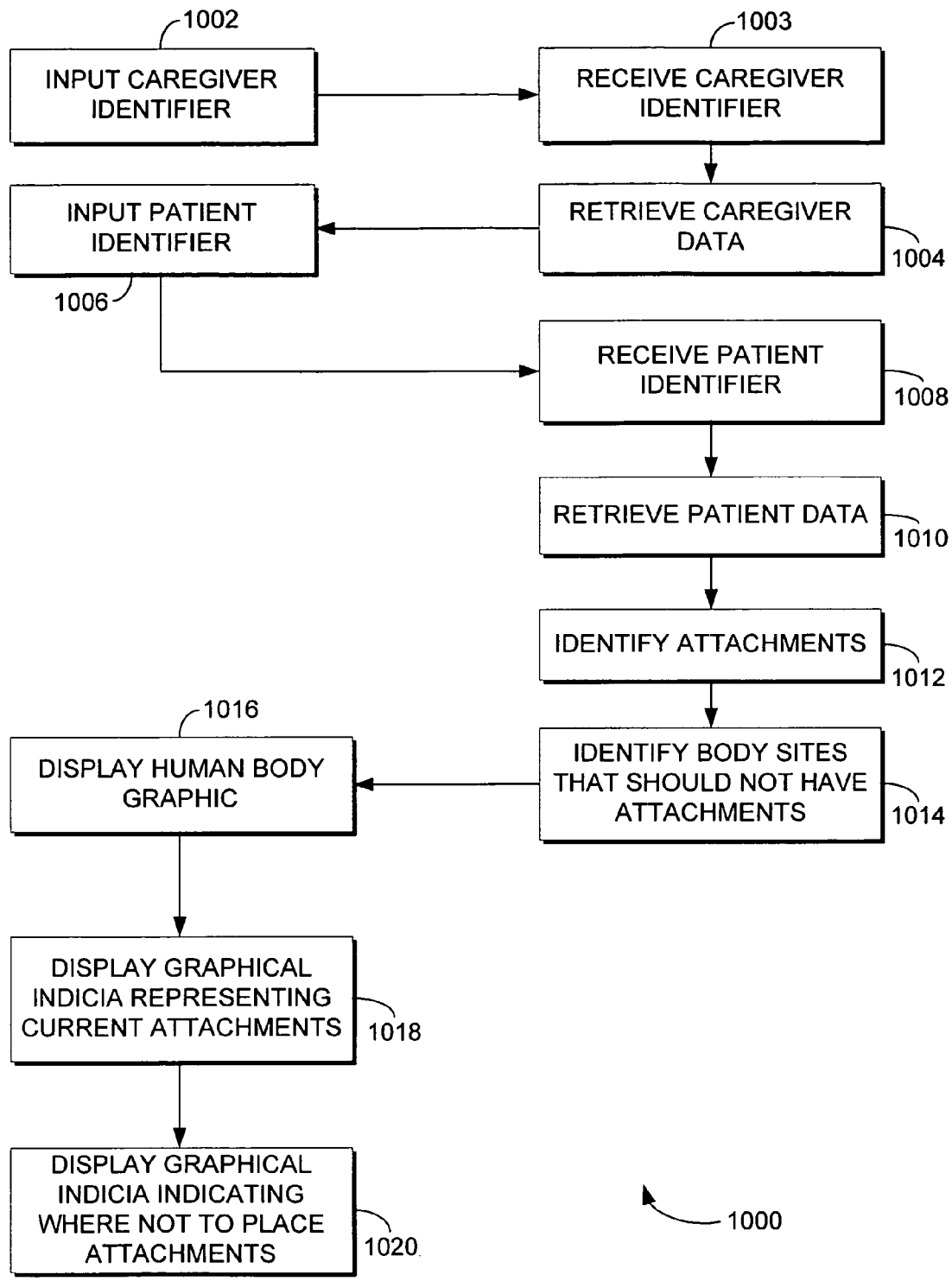
FIG. 10 is a flow chart illustrating a method for displaying graphical indicia representing current attachments and locations where attachments should not be placed in accordance with an embodiment of the present invention.

With reference to FIG. 10, a method 1000 in a computerized healthcare environment for displaying graphical indicia on a human body representation, the human graphical indicia indicating locations of existing attachments or location of where attachments cannot or should not be placed is shown. FIG. 10 illustrates further details of a method for using the system of the invention in a healthcare environment. At step 1002, a caregiver identifier is input. In one embodiment, the caregiver performs self-authentication by scanning the caregiver identifier with the caregiver portable computing device. As set forth above, this step may involve swiping or sensing a barcode, RFID, or other machine readable identifier on the caregiver security badge. This identifies the caregiver. However, one of skill in the art will appreciate that the caregiver identifier may be input in any variety of ways.

At step 1003, the caregiver identifier is received by the central information system. At step 1004, caregiver data are retrieved and verification to determine whether the caregiver is authorized to access information about the patient is performed. At step 1006, the patient identifier is input into the system. In one embodiment, the caregiver scans the patient identifier with the caregiver portable computing device. This step may involve swiping or sensing a barcode, RFID, or other machine readable identifier. In one embodiment, the identifier may be located on a patient identification bracelet or on a patient link micro-server.

At step 1008, the patient identifier is received by the central information system. At step 1010, patient data are accessed and retrieved. The patient information may be contained in a patient's electronic medical record. At step 1012, current attachments for the patients are determined and identified. At step 1014 it is determined whether there are one or more body site locations for the patient where attachments cannot or should not be placed.

At step 1016, a representation of at least a portion of the human body for the patient is displayed. For instance, the representation may be displayed on a caregiver portable computing device or any other display. At step 1018, at least one graphical indicia indicating the location of an existing attachment to the patient is displayed on the representation of the human body. The graphical indicia are plotted on the representation of the human body in the same or similar location that the attachment is attached to the patient as described with reference to FIG. 12 below. At step 1020, at least one graphical indicia indicating a location where an attachment cannot or should not be placed is displayed on the human body representation for the patient. The graphical indicia are plotted on the representation of the human body in the same or similar location where the attachment cannot or should not be attached to the patient.

Figure 12:
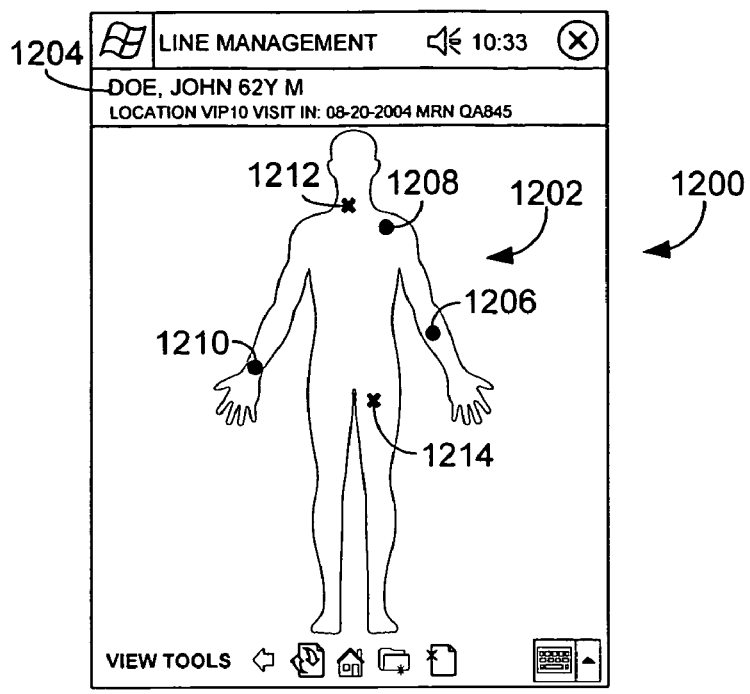

With reference to FIG. 12, a screen 1200 displaying a human body representation 1202 is shown. The human body representation 1202 is shown for fictitious patient John Doe 1204. Graphical indicia 1206, 1208 and 1210 represent attachments currently attached to patient 1204. Graphical indicia 1206 represents a peripheral catheter at the antecubital body site location. Graphical indicia 1208 represents a subclavian or central line at the subclavian body site location and graphical indicia 1210 represents an arterial attachment at the radial body site location.

Also displayed on the human body representation 1202 are graphical indicia 1212 and 1214 representing body site locations where attachments cannot or should not be placed. Graphical indicia 1212 represents the jugular body site location and graphical indicia 1214 represents the femoral body site location. In this example, graphical indicia 1212 and 1214 indicate that attachments should not be placed in these locations of patient 1204 because the sites are in use. In this embodiment, the graphical indicia used to represent current attachment body site location and locations where attachments cannot or should not be placed are different.

Figure 11:
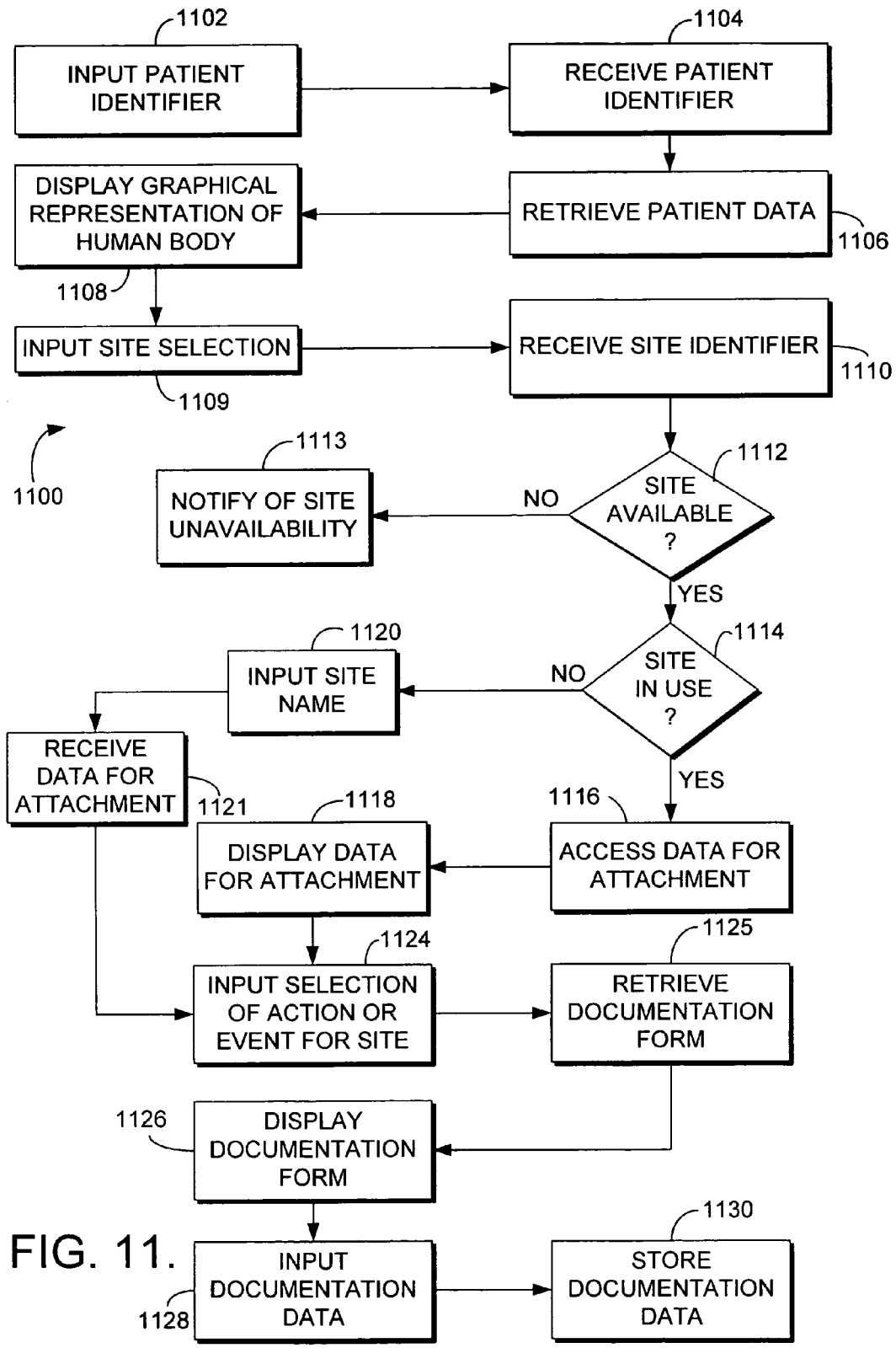
FIG. 11 is a flow chart illustrating a method for determining whether a body site location for a patient is available in accordance with an embodiment of the present invention.

Turning now to FIG. 11, a method 1100 for determining whether a body site location of a patient is available for an attachment. At step 1102, a patient identifier is input. In one embodiment, the caregiver scans the patient identifier with the caregiver portable computing device. This step may involve swiping or sensing a barcode, RFID, or other machine readable identifier. In one embodiment, the identifier may be located on a patient identification bracelet or on a patient link micro-server. At step 1104, the patient identifier is received by the central information system. At step 1106, patient information is accessed. The patient information may be contained in a patient's electronic medical record.

At step 1108, a representation of least a portion of a human body for the patient is displayed. At step 1109, a site selection is input by a caregiver. At step 1110 the selection of a location on the representation of the human body is received. For example, if a caregiver wants to administer a consumable or place an attachment on the patient at a particular body site location, the caregiver would select the location on the human body representation corresponding to the body site location for administration. With reference to FIG. 12, the caregiver would select the jugular body site location 1212 on the human body representation 1202 if the caregiver wanted to administer inotropic to the patient using the jugular body site location 1212.

Referring again to FIG. 11, after receiving the selection of the body site location, at step 1112 it is determined whether any attachments may be properly or safely attached, inserted, laid upon or physically associated with the identified body site of the patient. For example, it may be determined that any attachments may not be safely associated with a body site for the patient due to the patient's medical condition or other attachments associated with the identified body site for the patient. If it is determined that attachments may not be properly or safely attached to the body site location selected, at step 1113, notification of the body site unavailability for attachments is displayed. In one embodiment, the notification that attachments may not be properly or safely associated with the body site of the patient is displayed on a caregiver portable computing device. The notification may be in the form an alert or alarm.

Figure 13:
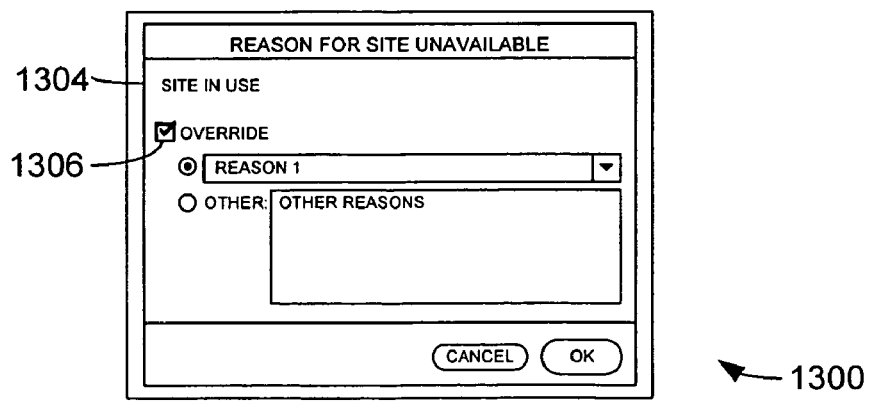

With reference to FIG. 13, a screen 1300 displaying a notification of the body site location unavailability for attachments is shown. This exemplary screen displays reason 1304 for the unavailability of the body site location and the ability for a caregiver to override 1306. Screen 1300 allows the caregiver to input the reason for overriding 1306 the unavailability of the body site. In one embodiment, if the caregiver chooses to override the notification, the caregiver scans the caregiver identifier. The caregiver's override is received by the central information system and the override information is stored.

Referring again to FIG. 11, if the body site location selected is available for attachments, at step 1114 it is determined whether an attachment already exists at the body site location. For example, with reference to FIG. 14, if body site location 1410 was selected, it would be determined that an attachment already exists at the body site location. However, if a body site location without graphical indicia is selected, it is determined that an attachment does not exist for the patient at that body site location.

Figure 16:
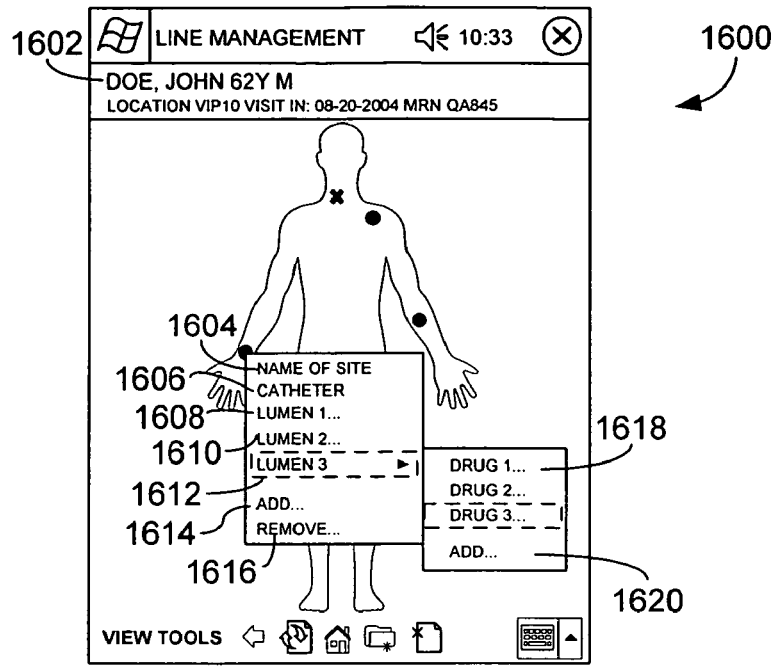

With reference to FIG. 11, if it is determined that an attachment already exists at the selected body site location, at step 1116, data for the attachment is obtained. The data obtained for the attachment may include femoral line in place. The data obtained at step 1116 is displayed at step 1118. The data for the attachment may be displayed in any variety of ways, including on a caregiver portable computing device or a computer screen display. After the data for the attachment are displayed the system proceeds to step 1124. An exemplary screen 1600 displaying attachment data is shown in FIG. 16. For a patient 1602 the attachment data includes the name of the body site location 1604, the type of attachment 1606, the components of the attachment 1606, 1608 and 1610. Whether a component is being added 1614 or removed 1616 from the documentation. The data also may include drugs or consumables 1618 that may be added 1620 to the component 1612 of the attachment 1606.

Figure 14:
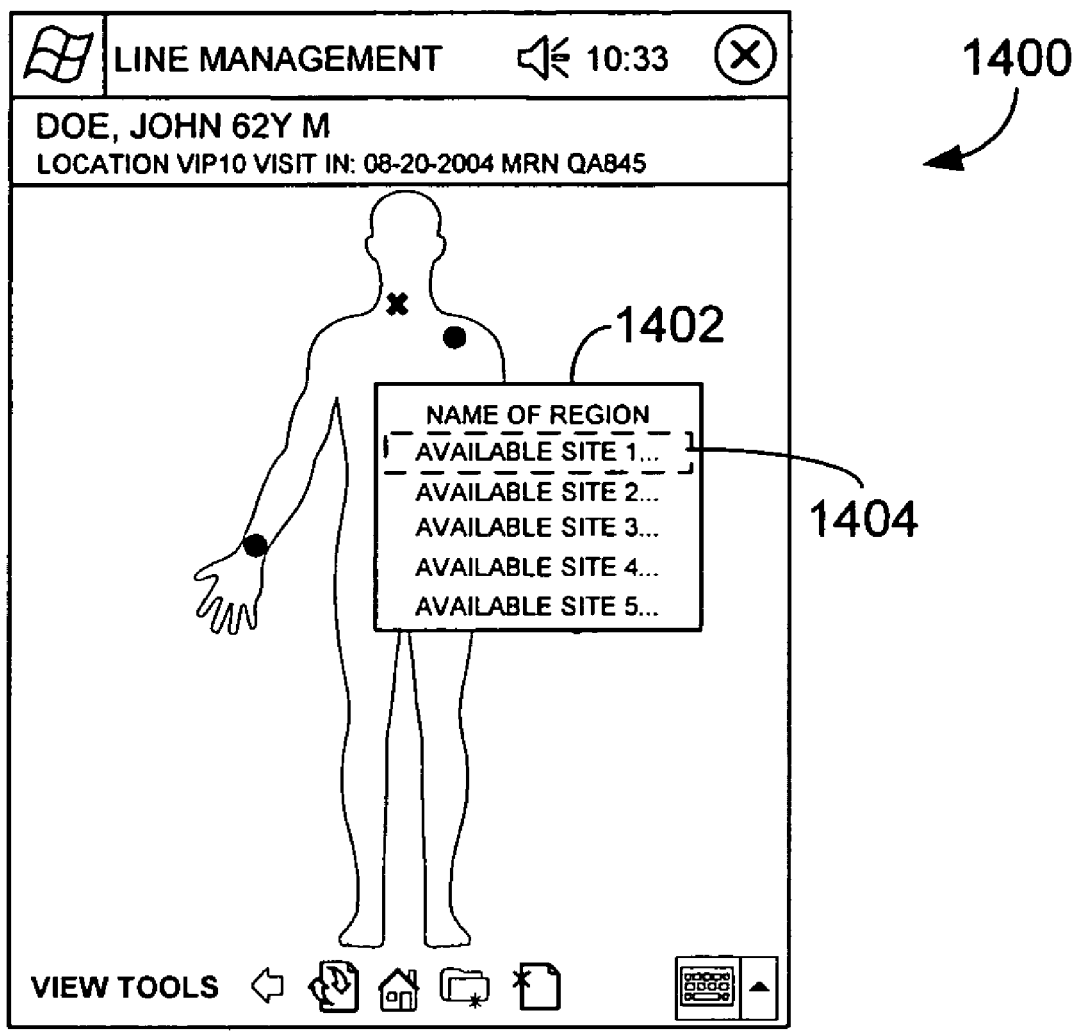

Referring again to FIG. 11, if at step 1114 it is determined that an attachment does not already exist at the body site location selected at step 1120, then the name of the body site is input. With reference to FIG. 14, a screen 1400 displaying a pre-defined list 1402 of body site location names 1404 is shown. A caregiver can chose the correct body site location name for the body site location from the list 1402. Alternatively, a caregiver can manually enter in the name of the selected body site location name or by scanning a bar code identifier identifying the body site location.

Figure 15:
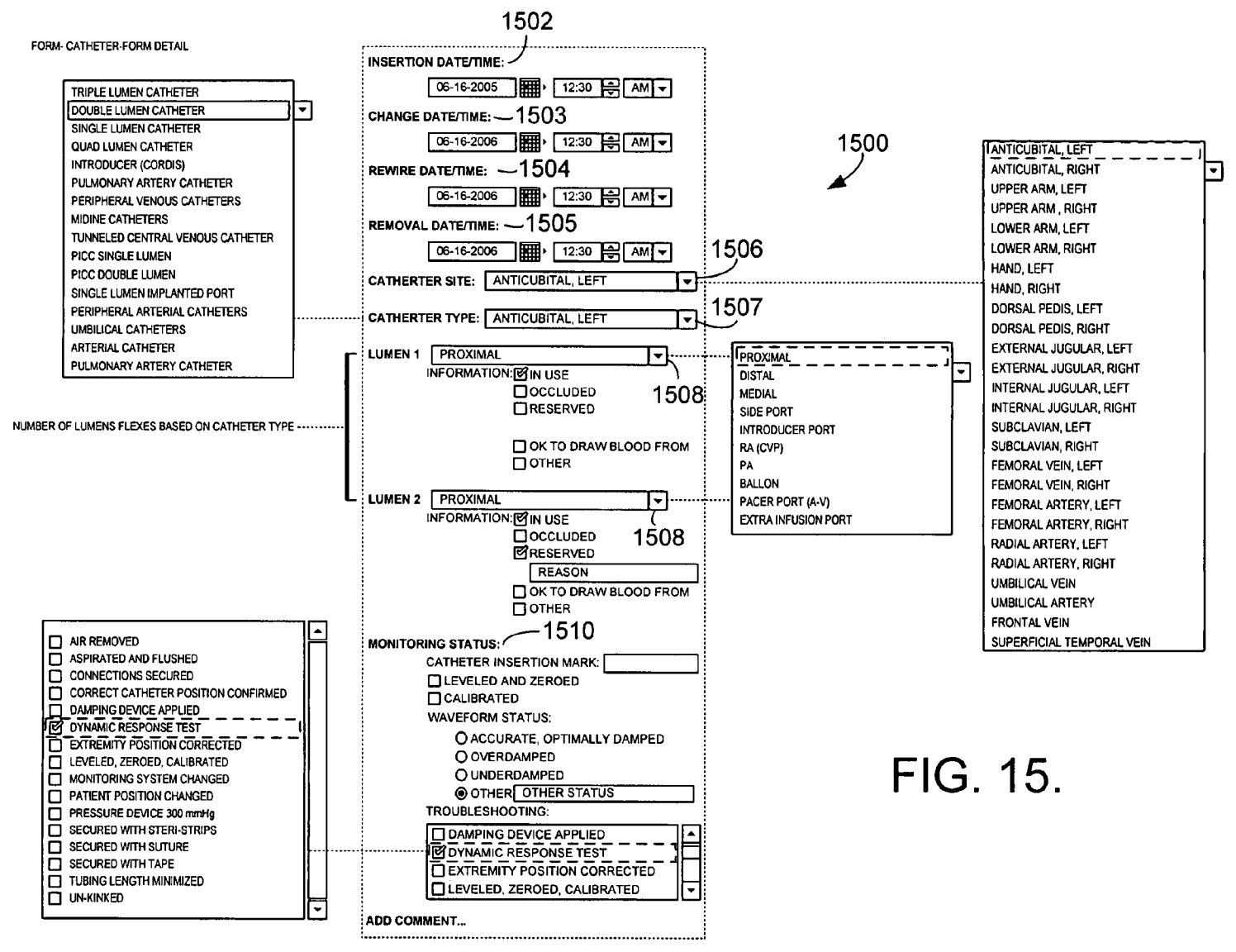

Referring again to FIG. 11, at step 1121 data related to the attachment to be associated with the body site location are received. Information for the attachment may be received in a variety of ways. Information may be received by scanning an identifier on the attachment, accessing a database with information for attachment and storing the information for the attachment. Alternatively, information may be input by a caregiver. With reference to FIG. 15, an exemplary screen 1500 displaying information to be input for the attachment is shown. The information includes the insertion date/time 1502, the attachment site 1506, the type of attachment 1507, information regarding subcomponents for the attachment 1508, such as lumens for a catheter. Screen 1500 may also be used for updating information for an existing attachment including the change date/time 1503, rewiring date/time 1504, removal date/time 1505 and monitoring information 1510.

Figure 17:
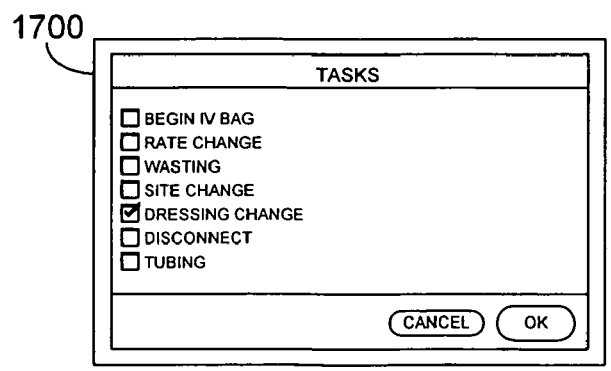

Referring to FIG. 11, at step 1124, the action or task to be completed for the body site is received. In one embodiment, the action or task may be selected from a list of tasks 1700 as shown in FIG. 17. Actions may include, but are not limited to, beginning an IV bag, a rate change for the IV pump, a bolus or infuse event, a wasting event, a site change, a dressing change for the site, tubing events and disconnecting events. Actions may include any event associated with care provided related to an attachment. At step 1125, a documentation form for the selected action is retrieved and is displayed at step 1126. Exemplary action documentation forms are shown in FIGS. 18-27. At step 1128 documentation data for the task or event is input by a caregiver and is stored at step 1130.

Figures 18, 19:
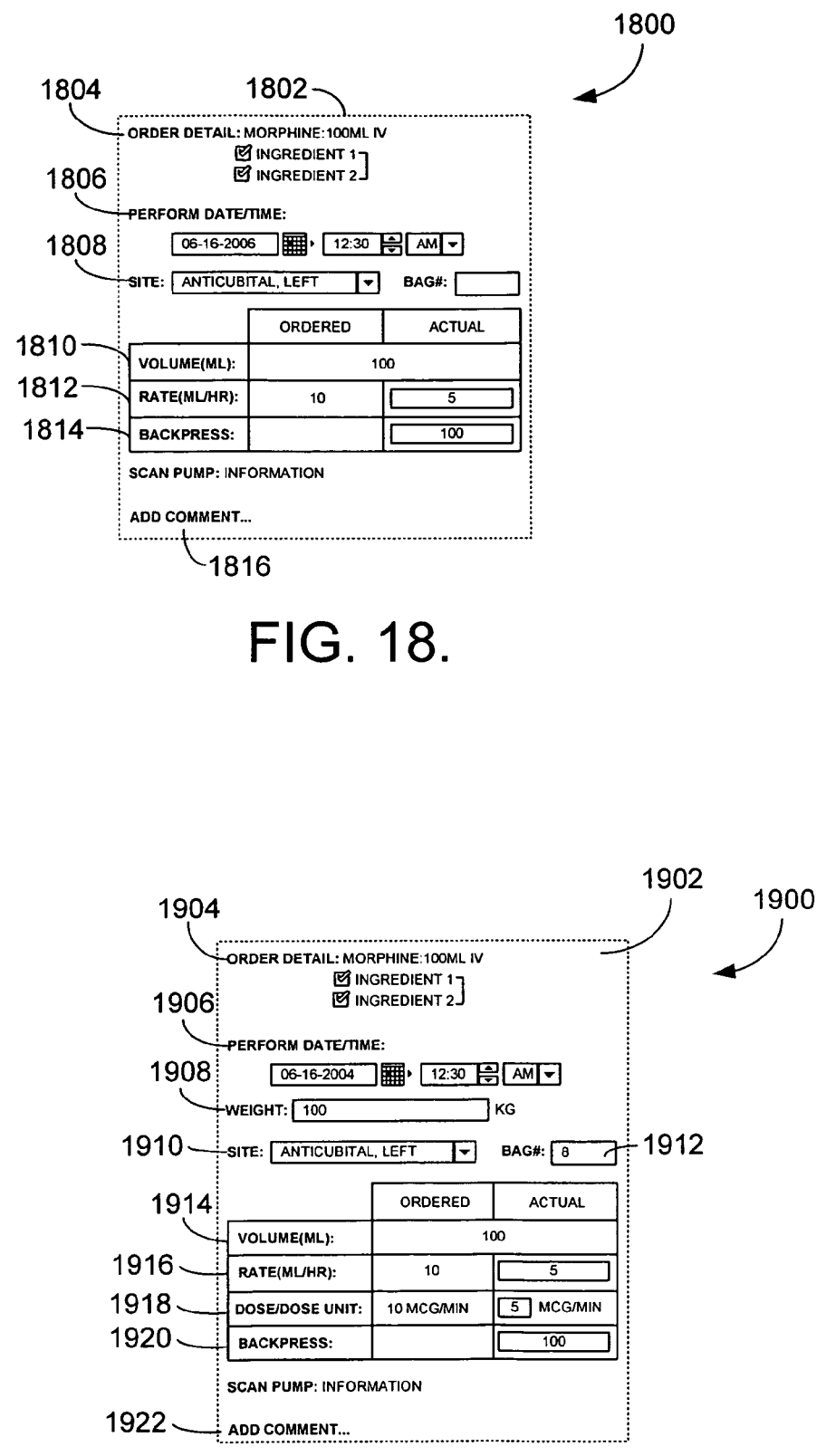

With reference to FIG. 18, a screen 1800 displaying a documentation form 1802 for documenting the beginning an IV bag attached to a body site is shown. Data that may be documented for the IV bag in the exemplary screen includes the order details 1804, date and time of beginning the bag 1806, the site name 1808 and the volume 1810, rate 1812 and backpress 1814 of the bag. Furthermore, a caregiver may input additional comments 1816 for the action if needed.

With reference to FIG. 19, a screen 1900 displaying a documentation form 1902 for documenting beginning an IV bag attached to a body site with weight based dosing is shown. Data that may be documented for the IV bag in the exemplary screen includes the order detail 1904, performance date and time 1906, weight in kilograms 1908, the site name 1910, the bag number 1912, the volume 1914, rate 1916, dose unit 1918 and backpress 1920 of the bag. A caregiver may input addition comments and information 1922 for the action if needed.

With reference to FIG. 20, a screen 2000 displaying a documentation form 2002 for documenting a rate change of an IV bag is shown. Data that may be documented for the action on the exemplary screen includes the order detail 2004, performance date and time 2006, site location 2008, bag number 2009, the volume 2010 and rate 2012 of the bag. Additional comments and information 2014 may also be input by the caregiver.

With reference FIG. 21, a screen 2100 displaying a documentation form 2102 for documenting a rate change of an IV bag with weight based dosing is shown. Data that may be documented for the action on the exemplary screen includes the order detail 2104, performance date and time 2106, weight 2108, site 2109, bag number 2110 and the volume 2112, rate 2114, and dose 2116 of the bag. Additional information and comments 2118 may also be input as needed.

With reference to FIG. 22, a screen 2200 displaying a documentation form 2202 for documenting a bolus or infusion event is shown. Data that may be documented for the event on the exemplary screen includes the order detail 2204, site 2206, bag number 2208, beginning of infusion time 2210, end of infusion time 2212, the infuse over 2214, volume 2216 and rate 2218 of the bag. Additional information or comments 2220 may also be input.

With reference to FIG. 23, a screen 2300 displaying a documentation form 2302 for documenting a wasting event is shown. Data that may be documented for the event on the exemplary screen includes the order detail 2304, the waste volume 2306, bag number 2308, date and time of the event 2310. Additional information or comments 2312 may also be input.

Referring to FIG. 24, a screen 2400 displaying a documentation form 2402 for documenting a site change is shown. Data that may be document for the site change event on the exemplary screen includes the order detail 2404, performance date and time 2406, site the caregiver is changing to 2408 and the bag number 2410. A caregiver may also enter additional information or comments 2412 for the event.

Figure 25:
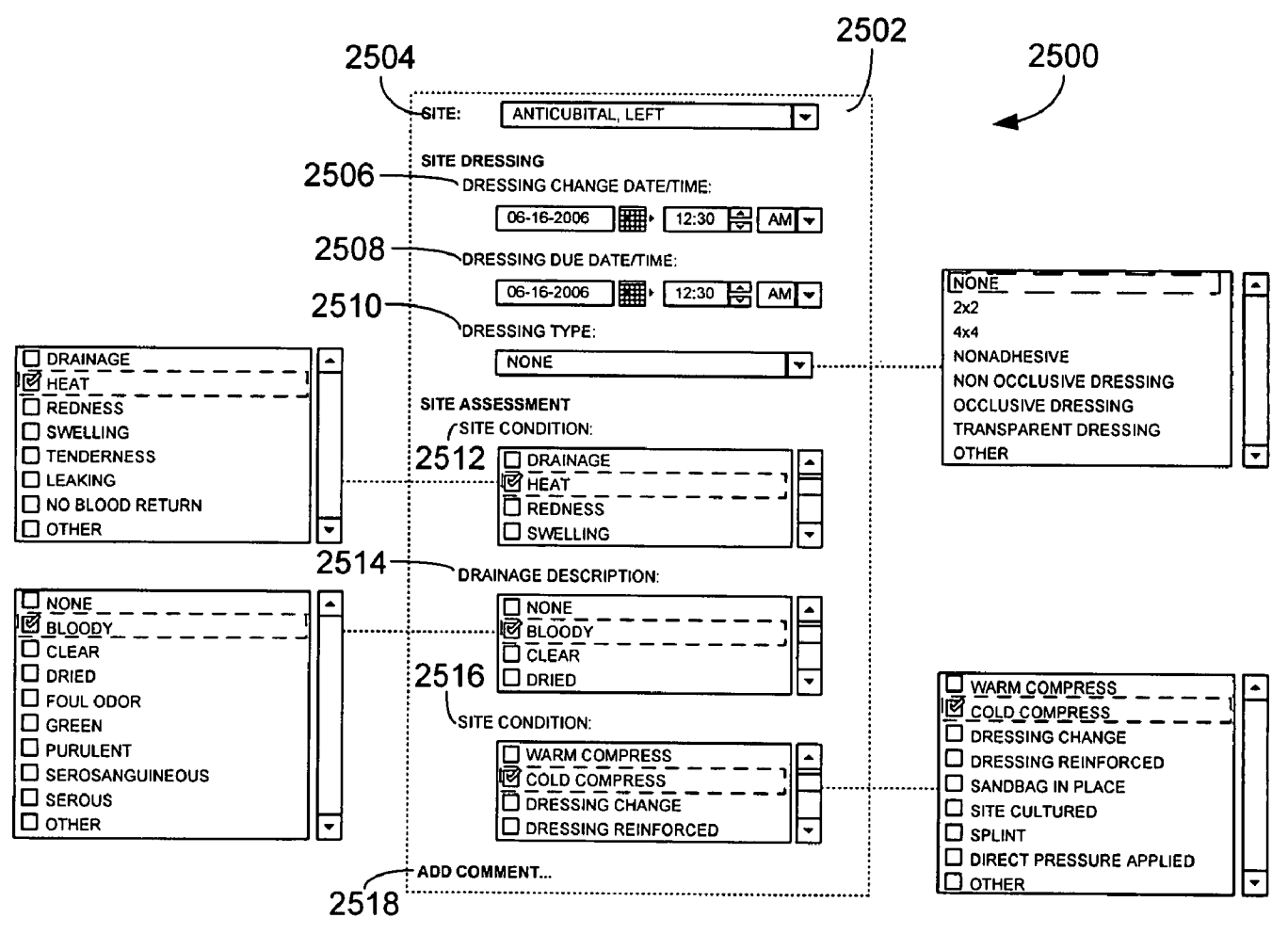

With reference to FIG. 25, a screen 2500 displaying a documentation form 2502 for documenting a dressing change at a body site is shown. Data that may be documented for the dressing change even on the exemplary screen includes the site name 2504, the dressing change date and time 2506, the dressing due date and time 2508, the dressing type 2510, the site condition 2512, a description of the drainage at the site 2514 and any site interventions 2516. A caregiver may also enter additional information or comments 2518 for the event.

Figure 26:
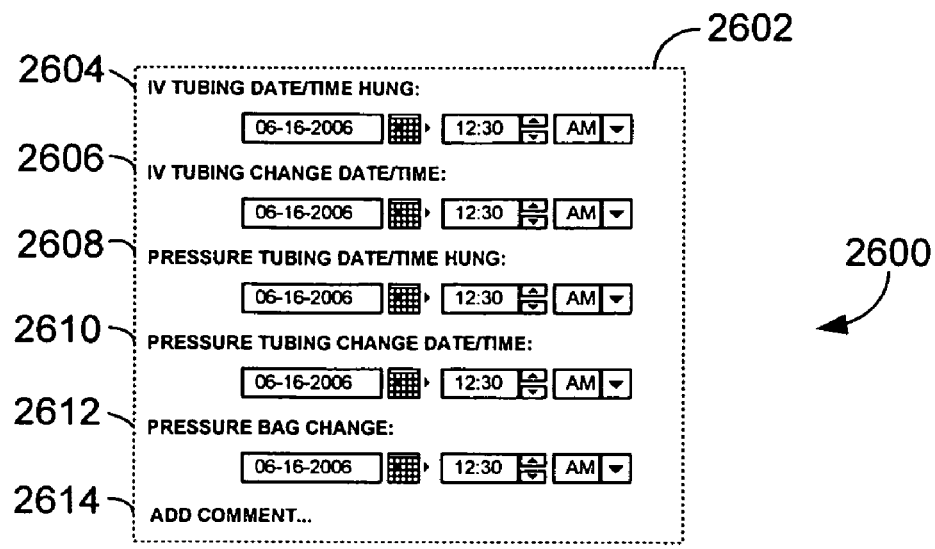
Figure 27:
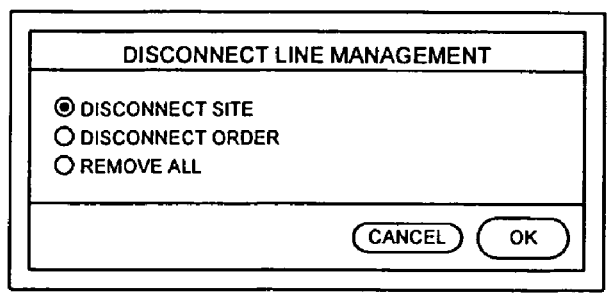

With reference to FIG. 26, a screen 2600 displaying a documentation form 2602 for documenting a tubing event is shown. Data that may be documented for tubing includes the date and time IV tubing was hung 2604, the date and time IV tubing was changed 2606, the date and time pressuring tubing was hung 2608, the date and time pressuring tubing was changed 2610 and the date and time of pressure bag change 2612. A caregiver may also enter additional information or comments 2614 relating to the event. FIG. 27 is an illustrative screen display of a form for line management disconnection.

Using the above-described system and method, patient, caregiver, body site, attachment and consumable identifiers are recorded on the caregiver portable computing device and transmitted to the central information system 20 either through the patient-link server 98 or directly. Caregivers have no opportunity to record data inaccurately as with currently existing systems. Using network capabilities, a single caregiver can monitor multiple parameters for dozens of patients. The presently disclosed system can be used to help monitor resources and allows less skilled personnel to handle routine tasks. The invention is not limited to use in any particular setting. It can be used in any setting in which multiple patients or caregivers are present.

The disclosed system is safer more efficient that currently used systems because it eliminates unnecessary steps. With the disclosed system, a caregiver can receive directions at a patient's bedside by scanning barcodes or recognizing other machine-readable identifiers. The scanning creates the documentation and eliminates the need for an additional process.

While particular embodiments of the invention have been illustrated and described in detail herein, it should be understood that various changes and modifications might be made to the invention without departing from the scope and intent of the invention. For example, a traditional personal computer (as opposed to a handheld device) may be located at the bedside and equipped with a reader device. The embodiments described herein are intended in all respects to be illustrative rather than restrictive. Alternate embodiments will become apparent to those skilled in the art to which the present invention pertains without departing from its scope.

From the foregoing it will be seen that this invention is one well adapted to attain all the ends and objects set for above, together with other advantages, which are obvious and inherent to the system and method. It will be understood that certain features and sub-combinations are of utility and may be employed without reference to other features and sub-combinations. This is contemplated and within the scope of the appended claims.

The invention claimed is:

1. A method in a computerized health care environment for determining whether an attachment may be safely attached to a body site of a patient, the method comprising:

receiving a patient identifier to identify a patient;

receiving an attachment identifier identifying an attachment;

receiving a body site identifier identifying the area of the body of the patient to which the attachment is to be placed;

determining whether the attachment may be safely attached to the body site of the patient; and displaying a tangible notification indicating whether the attachment may be safely attached to the body site of the patient.

2. The method of claim 1, wherein the patient identifier is a bar code scanned with a portable information device.

3. The method of claim 1, wherein the attachment identifier is a bar code scanned with a portable information device.

4. The method of claim 1, wherein the body site identifier is a bar code scanned with a portable information device.

5. The method of claim 1, wherein if it is determined that the attachment may be safely attached to the body site of the patient, notifying the caregiver of such.

6. The method of claim 1, wherein if it is determined that the attachment may not be safely attached to the body site of the patient, notifying the caregiver of such.

7. The method of claim 6, wherein the notification is displayed on a portable information device.

8. The method of claim 1, further comprising accessing the patient's electronic medical record and data for the attachment or body site to determine whether the attachment may be safely attached to the body site of the patient.

9. The method of claim 1, wherein an attachment is an apparatus physically associated with the patient.

10. A computerized system for collecting data from a patient identifier, an attachment identifier, and a body site identifier, the system comprising:
- an information system containing patient data, attachment data and body site data;
- a patient identifier linking a patient to patient data in the central information system;
- an attachment identifier linking the attachment to attachment data in the central information system;
- a body site identifier identifying a body site location on the patient and linking the site to location data in the central information system; and
- an information device for collecting the patient identifier, the attachment identifier and the body site identifier and communicating with the central information system to access the patient data, attachment data and body site data.

11. The system of claim 10, further comprising:
- a consumable identifier linking the consumable to consumable data in the central information system.

12. The system of claim 11, wherein the patient data, attachment data and body site data from the information system are utilized to determine whether the attachment may be safely attached to the body site of the patient.

13. The system of claim 10, wherein the patient identifier, attachment identifier and body site identifier are bar codes scanned with the portable information device.

14. The system of claim 10, wherein an attachment is an apparatus physically associated with the patient.

15. A method of retrieving and transmitting patient data in a computerized environment, the method comprising:
- retrieving a patient identifier with a portable information device, wherein the patient identifier identifies a patient;
- retrieving an attachment identifier with a portable information device, wherein the attachment identifier identifies an attachment;
- retrieving a body site identifier with a portable information device, wherein the body site identifier identifies a location for the attachment on the patient's body;
- communicating the patient identifier, the attachment identifier and the body site identifier to a central information system; and
- receiving current patient related information from the central information system at the portable information device.

16. The method of claim 15, wherein the current patient related information from the central information system at the portable information device comprises data identifying whether the attachment may be safely attached to the body site of the patient.

17. The method of claim 15, wherein the patient identifier is a bar code scanned with a portable information device.

18. The method of claim 15, wherein the attachment identifier is a bar code scanned with a portable information device.

19. The method of claim 15, wherein the body site identifier is a bar code scanned with a portable information device.

20. The method of claim 15, wherein an attachment is an apparatus physically associated with the patient.

* * * * *